(12) United States Patent
Tanaka et al.

(10) Patent No.: US 6,528,479 B1
(45) Date of Patent: *Mar. 4, 2003

(54) DOMINANT NEGATIVE MUTANTS OF IRS-1 AND USES THEREOF

(75) Inventors: Shinji Tanaka, Charlestown, MA (US); Jack R. Wands, Waban, MA (US)

(73) Assignee: The General Hospital Corporation, Boston, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/964,296

(22) Filed: Nov. 4, 1997

Related U.S. Application Data

(60) Provisional application No. 60/030,129, filed on Nov. 4, 1996.

(51) Int. Cl.[7] .................. A01N 37/18; A61K 38/00; A61K 38/28; C07K 1/00

(52) U.S. Cl. ................ 514/2; 514/3; 530/350

(58) Field of Search .............................. 530/350; 514/2, 514/3

(56) References Cited

FOREIGN PATENT DOCUMENTS

WO   WO 94/29345   * 12/1994

OTHER PUBLICATIONS

Zhou et al (Nat. Struct. Biol. vol. 3(4) pp 388–393), 1996.*
Paz et al (J. of Biological Chem. vol. 271(12) pp 6998–7003), Mar. 22, 1996.*
Araki et al., "Alternative pathway of insulin signalling in mice with targeted disruption . . . ", Nature 372:186–190, 1994.
Bhavani et al., "Effect of Ethanol on Tyrosyl Phosphorylation of Insulin Receptor Substrate . . . ", Abstract 253, Hepatology, No. 120A, AASLD Abstracts, 1993.
Bhavani et al., "Increased Tyrosyl Phosphorylation of Insulin Receptor Substrate–1 . . . ", Abstract 707, Hepatology 20, No. 4, Pt. 2, AASLD Abstracts, 273A, 1994.
Bhavani et al., "Effect of Ethanol on p36 Protein Kinase Substrate and Insulin Receptor . . . ", Alcoholsim: Clinical and Experimental Research 19:441–446, 1995.
D'Ambrosio et al., "Transforming Potential of the Insulin Receptor Substrate 1[1]", Cell Growth & Differentiation 6:557–562, 1995.
Furusaka et al., "Expression of insulin receptor substrate–1 in hepatocytes: an investigation . . . ", Cancer Letters 84:85–92, 1994.
Gustafson et al., "Phosphotyrosine–Dependent Interaction of SHC and Insulin Receptor . . . ", Molecular and Cellular Biology 15:2500–2508, 1995.
Harlan et al., "Pleckstrin homology domains bind to phosphatidylinositol–4,5–bisphosphate", Nature 371:168–170, 1994.
Ito et al., "Overexpression of Human Insulin Receptor Substrate 1 Induces Cellular Transformation . . . ", Molecular and Cellular Biology 16:943–951, 1996.
Ito et al., "Role of Signal Transduction Pathways in Hepatic Transformation . . . ", Abstract 371, Hepatology 22, No. 4, Pt. 1, 199A, 1995.
Ito et al., "Overexpression of the Human Insulin Receptor Substrate–1 . . . ", Abstract 706, Hepatology 20, No. 4, Pt. 2, 273A, 1994.
Kaleko et al., "Overexpression of the Human Insulinlike Growth Factor I . . . ", Molecular and Cellular Biology 10:464–473, 1990.
Kavanaugh et al., "An Alternative of SH2 Domains for Binding Tyrosine–Phosphorylated Proteins", Science 266:1862–1865, 1994.
Kuhne et al., "Dephosphorylation of Insulin Receptor Substrate 1 by the Tyrosine . . . ", Journal of Biological Chemistry 269:15833–15837, 1994.
Kuhne et al., "The Insulin Receptor Substrate 1 Associates with the SH2–containing . . . ", Journal of Biological Chemistry 268:11479–11481, 1993.
Myers et al., "The IRS–1 Signaling System", TIBS 19:289–293, 1994.
Myers et al., "The Pleckstrin Homology Domain in Insulin Receptor Substrate–1 Sensitizes . . . ", Journal of Biological Chemistry 270:11715–11718, 1995.
Nishiyama et al., "Cloning and Increased Expression of an Insulin Receptor . . . ", Biochem. and Biophys. Res. Com. 183:280–285, 1992.
Pawson, T., "Protein Modules and Signalling Networks", Nature 373:573–579, 1995.
Platanias et al., "The Type I Interferon Receptor Mediates Tyrosine Phosphorylation . . . ", Journal of Biological Chemistry 271:278–282, 1996.
Sasaki et al., "Expression and Phosphorylation of Insulin Receptor Substrate 1 during . . . ", Journal of Biological Chemistry 268:3805–3808, 1993.
Sun et al., "Role of IRS–2 in insulin and cytokine signalling", Nature 377:173–177, 1995.
Sun et al., "Pleiotropic Insulin Signals Are Engaged by Multisite . . . ", Molecular and Cellular Biology 13:7418–7428, 1993.

(List continued on next page.)

*Primary Examiner*—Mark Navarro
(74) *Attorney, Agent, or Firm*—Fish & Richardson, P.C.

(57) ABSTRACT

Dominant negative mutants of mammalian IRS-1 proteins and therapeutic compositions containing such mutants. Also featured are methods of using the dominant negative mutants to inhibit tyrosyl phosphorylation of endogenous IRS-1 in mammalian cells and methods of treating a mammalian malignancy in which tyrosyl phosphorylation of endogenous IRS-1 plays a causative role.

6 Claims, 1 Drawing Sheet

OTHER PUBLICATIONS

Tamemoto et al., "Insulin resistance and growth retardation in mice . . . ", Nature 372:182–186, 1994.

Tanaka et al., "Cellular Transformation Induced by Insulin Receptor Substrate . . . ", Abstract 509, Hepatology, AASLD Abstracts, 234A, 1995.

Tanaka et al., "Neoplastic Transformation Induced by Insulin Receptor Substrate–1 . . . ", Journal of Biological Chemistry 271:14610–14616, 1996.

Touhara et al., "Binding of G Protein beta–gamma–Subunits to Pleckstrin Homology Domains", Journal of Biological Chemistry 269:10217–10220, 1994.

Yonezawa et al., "Signal Transduction Pathways from Insulin Receptors to Ras", Journal of Biological Chemistry 269:4634–4640, 1994.

Haft et al., "Deletion of 343 Amino Acids for the Carboxyl Terminus of the β–Subunit of the Insulin Receptor . . . ", Biochemistry 33:9143–9151, 1994.

Sanchez–Margalet et al., "Role of p85 Subunit of Phosphatidylinositol–3–Kinase as an . . . ", Molecular Endocrinology 9:435–442, 1995.

Yenush et al., "Functional Domains of the Insulin Receptor Responsible for Chemotactic Signaling", Journal of Biological Chemistry 269:100–104, 1994.

* cited by examiner

SEQUENCE LISTING

<160> NUMBER OF SEQ ID NOS: 5

<210> SEQ ID NO 1
<211> LENGTH: 4
<212> TYPE: PRT
<213> ORGANISM: Homo sapiens

<400> SEQUENCE: 1

Tyr Val Asn Ile
 1

<210> SEQ ID NO 2
<211> LENGTH: 4
<212> TYPE: PRT
<213> ORGANISM: Homo sapiens

<400> SEQUENCE: 2

Tyr Ile Asp Leu
 1

<210> SEQ ID NO 3
<211> LENGTH: 4
<212> TYPE: PRT
<213> ORGANISM: Homo sapiens

<400> SEQUENCE: 3

Tyr Met Pro Met
 1

<210> SEQ ID NO 4
<211> LENGTH: 4
<212> TYPE: PRT
<213> ORGANISM: Homo sapiens

<400> SEQUENCE: 4

Tyr Met Lys Met
 1

<210> SEQ ID NO 5
<211> LENGTH: 8
<212> TYPE: PRT
<213> ORGANISM: Homo sapiens

<400> SEQUENCE: 5

Asp Tyr Lys Asp Asp Asp Asp Lys
 1               5

DOMINANT NEGATIVE MUTANTS OF IRS-1 AND USES THEREOF

Under 35 USC §119(e) (1), this application claims the benefit of prior U.S. provisional application 60/030,129, filed Nov. 4, 1996.

STATEMENT AS TO FEDERALLY SPONSORED RESEARCH

The invention was funded in part by grants CA-35711 and AA-02666 from the National Institutes of Health. The government may have certain rights in the invention.

FIELD OF THE INVENTION

This invention relates to signal transduction in mammalian cells.

BACKGROUND OF THE INVENTION

Human hepatocellular carcinoma (HCC) is one of the most common and least understood tumors. Although persistent hepatitis B and C virus infections are major risk factors for the development of this disease, little is known regarding cellular pathogenesis. Normal hepatocyte proliferation is regulated by several growth factors, of which insulin, epidermal growth factor (EGF), transforming growth factor α (TGFα) and hepatocyte growth factor (HGF) are believed to be the most important (Moradpour et al., IN: *Hepatology*, 3rd ed., W. B. Saunders, Philadelphia, Pa.). Such growth factors bind to hepatocyte cell surface receptors with intrinsic tyrosine kinase activity and initiate a series of protein phosphorylation events within the cells. Tyrosyl phosphorylation (TP) of downstream molecules transmits the mitogenic signals from the cell surface to the nucleus through several signal transduction pathways.

A cDNA encoding one of the key molecules involved in the insulin mediated signal transduction cascade, human insulin receptor substrate-1 (human IRS-1 or hIRS-1), has been found to be overexpressed at the protein and RNA levels in HCC cell lines and tumor tissues (Furusaka et al., *Mol. Cell Biol.* 11:4405–4414, 1991; Nishiyama et al., *Biochem. Biophys. Res. Commun.* 183:280–285, 1992). Tyrosine residues of IRS-1 are phosphorylated following cellular stimulation by ligands such as insulin; insulin-like-growth-factor 1 (IGF-1); interleukins 4, 9 and 13; interferons α and β; growth hormone; leukemia inhibitory factor; and tumor necrosis factor (Artersinger et al., *J. Biol. Chem.* 270:14685–14692, 1995; Guo et al., *J. Biol. Chem.* 271:615–618, 1996; Myers et al., *J. Biol. Chem.* 270:11715–11718, 1995; Platanias et al., *J. Biol. Chem.* 271:278–282, 1996; Welham et al., *J. Biol. Chem.* 270:12286–12296, 1995). Tyrosyl phosphorylated IRS-1 serves as a key "docking" protein. It transmits mitogenic or metabolic signals by interacting, through specific motifs, with downstream molecules containing the Src homology domain 2 ($SH_2$) (Sun et al., *Nature* 377:173–177, 1995). For example, the $^{897}$YVNI (SEQ ID NO:1) motif of hIRS-1 binds to the Grb2 adapter protein (Baltensperger et al., *Science* 260:1950–1952, 1993); the $^{1180}$YIDL (SEQ ID NO:2) motif binds to Syp phosphatase (also known as PTP1D, PTP2C, and SH-PTP2) (Kuhne et al., *J. Biol. Chem.* 268:11479–11481, 1993); and $^{613}$YMPM (SEQ ID NO:3) and $^{942}$YMKM (SEQ ID NO:4) motifs are the principal binding sites for the p85 subunit of phosphatidylinositol-3 kinase (PI3K) (Backer et al., *EMBO J.* 11:3469–3479, 1992; Myers et al., *Proc. Natl. Acad. Sci. USA* 89:10350–10354, 1992). While TP sites are recognized throughout the entire IRS-1 protein, the $SH_2$-binding domains are located only in the C-terminal region (Myers et al., *Trends Biochem. Sci.* 19:289–293, 1994). The N-terminal sequences, however, contain three important functional domains identified as a pleckstrin homology (PH) region, located at amino acid residues 9–117 (Musacchio et al., *Trends Biochem. Sci.* 18:343–348, 1993), and two regions homologous to a phosphotyrosine binding (PTB) domain, located at amino acid residues 161–317 (Sun et al., *Nature* 377:173–177, 1995) and at amino acid residues 314–463 (Gustafson et al., *Mol. Cell. Biol.* 15:2500–2508, 1995).

Normal hepatic growth has been associated with TP of IRS-1 and its subsequent interaction with $SH_2$-containing molecules such as Grb2 and PI3K during the G1 phase of the hepatocyte cell cycle following partial hepatectomy (Sasaki et al., *J. Biol. Chem.* 268:3805–3808, 1993). There is now evidence to support the hypothesis that IRS-1 may have transforming properties as well (D'Ambrosio et al., *Cell. Growth Differ.* 6:557–562, 1995; Ito et al., *Mol. Cell. Biol.* 16:943–951, 1996). Stable transfection and overexpression of the hIRS-1 gene in NIH 3T3 cells leads to increased TP of the protein, enhanced binding of the protein to Grb2 and Syp but not PI3K, and persistent activation of the downstream MAPK (mitogen-activated protein kinase) cascade. Such transfected cells develop a phenotype characterized by increased transformed foci formation, induction of anchorage independent cell growth, increased cell proliferation and formation of large tumors in nude mice (Ito et al., *Mol. Cell Biol.* 16:943–951, 1996). The functional domains of the hIRS-1 protein required for its transforming activity have been shown to reside in both the $^{897}$YVNI (SEQ ID NO:2) and $^{1180}$YIDL (SEQ ID NO:3) motifs (Tanaka et al., *J. Biol. Chem.*, 1996). Insulin and IGF-1 have been shown to act as dominant cellular mitogens for several different human tumors including HCC (Macaulay, *Br. J. Cancer* 65:311–320, 1992).

SUMMARY OF THE INVENTION

The present invention is based on the discovery of the functional domains of mammalian IRS-1's that are essential for insulin- and IGF-1-induced TP and for subsequent activation of downstream signal transduction molecules associated with tumorigenicity. Applicants have also discovered that a dominant negative mutant protein derived from hIRS-1 blocks TP of endogenous hIRS-1 protein and other substrates of insulin- or IGF-1- induced TP (e.g., Shc). This mutant protein also reverses the malignant phenotype of HCC cells.

Accordingly, the invention features dominant negative mutants of mammalian (e.g., human) IRS-1 proteins. The mutants, when co-expressed with a wild type IRS-1 in a cell, block the function of the wild type IRS-1 in the cell. Dominant negative mutants substitute for wild-type proteins implicated in pathogenicity and can counteract their pathogenic effects.

The mutants of the invention can contain the pleckstrin homology domain and the two phosphotyrosine binding domains of their corresponding wild type IRS-1's. For instance, a dominant negative mutant of human IRS-1 can contain 460 amino acid residues from the amino-terminal half (i.e., amino acid residues 1–621) of native IRS-1. The pleckstrin homology (PH) domain corresponds approximately to amino acid residues 9–117 of hIRS-1, and is believed to bring IRS-1 to close proximity to cell membranes on which insulin receptor resides. The two phosphotyrosine domains (PTB) correspond approximately to amino acid residues 161–314 and 315–463 of hIRS-1, respectively. The PTB domains, when bound to insulin receptor, become phosphorylated at their tyrosine residues. IRS-1 thus phosphorylated can transmit the signal from the insulin receptor via the IRS-1' SH$_2$-binding region to proteins residing downstream in the insulin/IGF-1 signal transduction pathway.

The mutant protein may also lack at least one or even all of the functional SH$_2$-binding motifs at its SH$_2$-binding region, so that the protein can no longer bind to the SH$_2$ domain of one or all of its adaptor proteins (e.g., Syp, Grb2, PI3K, or NCK). For instance, a dominant negative mutant of human IRS-1 may lack at least 300 amino acid residues from its carboxy-terminal half (i.e., amino acid residues 622–1243). It may even lack the last 727 amino acid residues of human IRS-1.

The mutant can additionally contain a heterologous sequence, i.e., a sequence not related to IRS-1, to facilitate its identification or purification. The heterologous sequence may contain an epitope to which an antibody can bind, or a ligand (e.g., a maltose-binding protein domain or a His tag) of any other receptor molecule (e.g., maltose or nickel). This sequence can range from, e.g., 4–25 amino acid residues in length, and replace 0–25 amino acid residues of the IRS-1 sequence in the mutant protein. It will typically be at one end of the mutant protein, but can be in the middle. Exemplary epitopes include FLAG, E-tag, c-myc tag, VSV-GP, T7 tag, HSV tag, and HA tag, all of which are well known in the art. The identity of the tag sequence is not critical.

Due to polymorphism that may exist at the IRS-1 genetic locus, minor variations in the amino acid sequence of the IRS-1's found in any given mammalian species may occur. For purposes of this invention, as long as adequate dominant negative effect on wild type IRS-1 remains, mutant proteins containing minor amino acid sequence variations as a result of natural IRS-1 polymorphism, or even as a result of recombinant genetic manipulation, are within the scope of this invention. In particular, one or all of the region corresponding to residues 118–160 of hIRS-1 (i.e., between the PH domain and the closest PTB domain) can be deleted or substituted with alternative residues. Preferably 0–35 of those residues would be deleted or substituted, and more preferably 0–25 (e.g., 0–10 or 0–5).

This invention also includes methods of inhibiting tyrosyl phosphorylation of an IRS-1 in a mammalian cell (e.g., a human hepatic cell). In these methods, an effective amount of a mutant of the invention is introduced into the cell (e.g., by expression from a recombinant expression construct within the cell). An effective amount is an amount that decreases the insulin- or IGF-1-induced TP of the endogenous IRS-1.

The dominant negative mutants of the invention can be used to reverse (e.g., eliminate or mitigate) a malignant phenotype of mammalian tumors (e.g., brain cancer, lung cancer, pancreatic cancer, and gastrointestinal cancers such as colon, liver cancer, or stomach cancer) in which hyperactivity of IRS-1 is known or believed to play a causative role. The malignant phenotype can be characterized by, e.g., growth without contact inhibition, anchorage-independent growth, increased rate of proliferation as compared to a normal cell, or ability to form a tumor in a nude mouse.

Also within the scope of the invention are therapeutic compositions containing a polypeptide of the invention, or a DNA encoding the polypeptide, admixed with a pharmaceutically acceptable carrier.

Unless otherwise defined, all technical and scientific terms used herein have the same meaning as commonly understood by one of ordinary skill in the art to which this invention belongs. Exemplary methods and materials are described below, although methods and materials similar or equivalent to those described herein can be used in the practice or testing of the present invention. All publications, patent applications, patents, and other references mentioned herein are incorporated by reference in their entirety. In case of conflict, the present specification, including definitions, will control. The materials, methods, and examples are illustrative only and not intended to be limiting.

Other features and advantages of the invention will be apparent from the following detailed description, and from the claims.

DETAILED DESCRIPTION OF THE INVENTION

Figure 1:
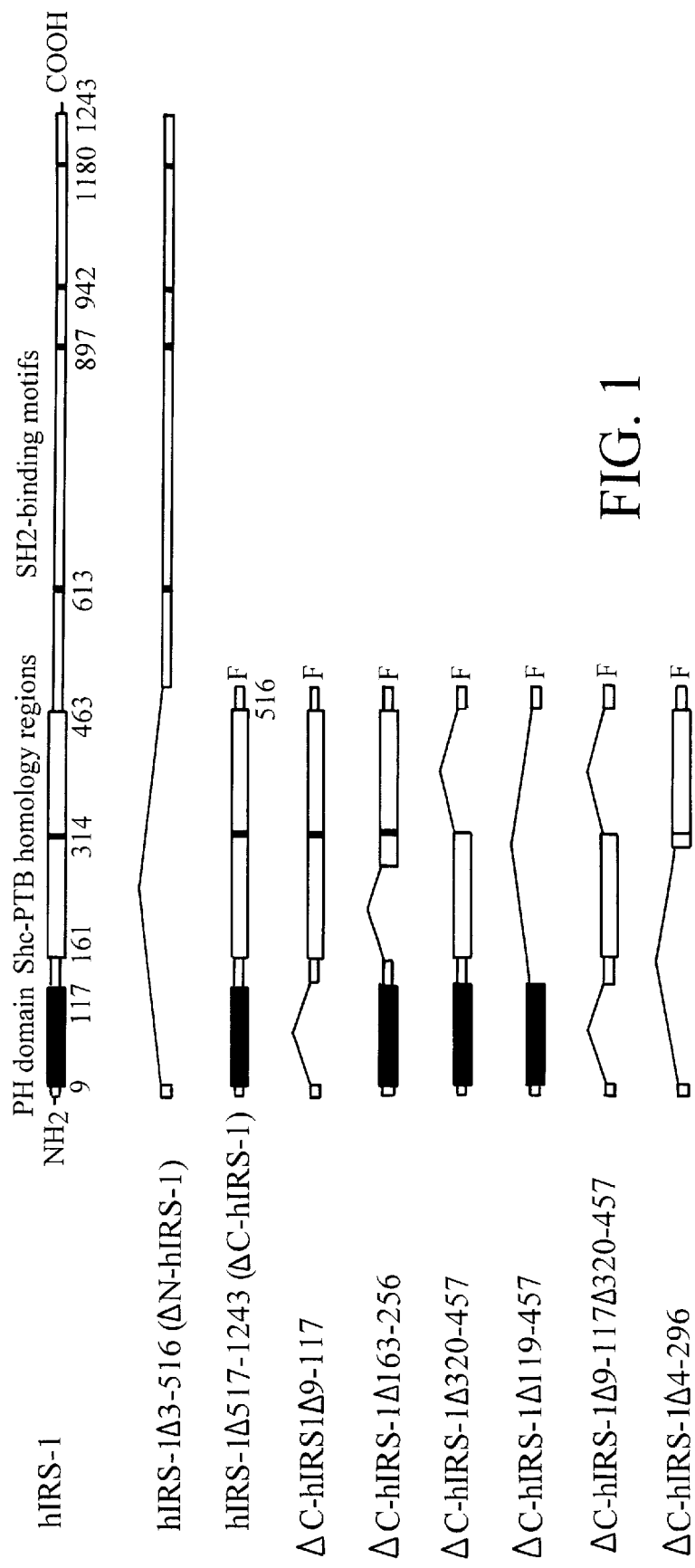
FIG. 1 is a schematic diagram showing the functional domains of the hIRS-1 protein and structures of the truncated mutants. The various C-terminal deletion mutants (i.e., the ΔC-hIRS-1 series) each contain a FLAG (F) epitope at the C-terminus. "PH" and "PTB" indicate pleckstrin homology and phosphotyrosine binding regions, respectively. "ΔN" and "ΔC" denote N- and C-terminal truncated mutants, respectively. The amino acid residues deleted in each mutant are indicated after the sign "Δ" in the name of the mutant.

Described in the Example below is one exemplary inhibitory protein of the invention. This protein, i.e., hIRS-1Δ517-1243, is a dominant negative mutant of hIRS-1, and consists of the 516 extreme N-terminal residues of wild type hIRS-1 and a FLAG epitope at its C terminus. In HCC cells expressing this protein, insulin- or IGF-1-mediated TP occurs on the mutant protein, while TP of endogenous hIRS-1, as well as of other substrates for insulin- or IGF-1-induced TP (e.g., Shc), is substantially decreased. Insulin- or IGF-1-mediated activation of other signal transducers such as MAPK and PI3K is also diminished. The HCC cells expressing this inhibitory protein display a loss of their tumorigenic phenotype. Additionally, while HCC cells form tumors in nude mice, the HCC cells expressing this protein do not. This Example demonstrates that dominant negative mutants of IRS-1 will be useful in the study and treatment of HCC.

As is shown in FIG. 1 and the Example described below, the amino-terminal and carboxy-terminal regions of IRS-1 perform different functions in the native molecule. The dominant negative mutants of the invention retain the functional properties of the amino-terminus, while shedding those of the carboxy-terminus. The amino-terminus, up to about amino acid residue 516 in hIRS-1, is the site of two activities which are important to retain in the mutant analogs of the invention: (i) it contains tyrosine residues which are tyrosine phosphorylated, at the expense of the tyrosine phosphorylation of the native molecule; and (ii) it contains the pleckstrin homology domain, which permits the mutant protein to be brought into close enough proximity to cell membranes to inhibit the tyrosine phosphorylation of endogenous hIRS-1. The carboxy-terminal SH$_2$-binding region encompasses functions which are abolished in the dominant negative mutants of the invention. These functions are (i) binding to the SH$_2$ domains in target molecules; and (ii) activating those molecules via such binding. The SH$_2$-binding region contains SH$_2$-binding motifs $^{897}$YVNI (SEQ ID NO:2), $^{1180}$YIDL (SEQ ID NO:3), $^{613}$YMPM (SEQ ID NO:4), and $^{942}$YMKM (SEQ ID NO:5), which bind respectively to Syp, Grb2, PI3K, and NCK. Preferably, in the dominant negative inhibitors of the invention, these motifs either have been deleted, or have been rendered unable to bind their respective receptors by amino acid substitutions that change the motifs' conformation.

In order to retain sufficient amino-terminal function for phosphorylation inhibition activity, the mutants of the invention should contain at least 315, more preferably 460, and even more preferably 516 amino acid residues of the 516 amino acid-long amino-terminus of hIRS-1. In order to abolish the SH$_2$-binding motifs, amino acids 517–1243 of the carboxy-terminal region of the molecule can be deleted or rendered inactive by critical amino acid substitutions or deletions.

Amino acid substitutions or deletions are permissible in the amino-terminal region as well, provided that the substitutions or deletions do not interfere with the enzymatically-driven phosphorylation reaction, or with the bringing of the mutant molecules into close proximity with cell membranes. The FLAG epitope can be eliminated or replaced with another epitope similarly designed to facilitate identification or purification of the mutant molecules.

Any mammalian cells that has an overactive IRS-1 signal transduction pathway (e.g., a signal transduction pathway activated by insulin, IGF-1, interferon, or growth hormone) can be treated with a mutant of the invention. Exemplary cells are tumor cells of the gastrointestinal system (e.g., tumor cells in esophagus, stomach, pancreas, gall bladder, liver, and colon), lung cancer cells, and brain tumor cells. Targeting of the inhibitory proteins to the cells may be achieved by local injection (e.g., into the hepatic portal vein for treatment of liver) of liposomes or other carriers (e.g., microspheres) that contain the inhibitory proteins. For enhanced targeting, the liposomes may be coated with molecules which function as ligands of tissue-specific receptors. An example of such a receptor is the hepatic asialoglycoprotein receptor, useful ligands of which include asialo-orosomucoid and (poly)L-lysine-asialo-orosomucoid (Spiess, Biochemistry 29(43):10009–10018, 1990; Wu et al., J. Biol. Chem. 267(18):12436–12439, 1992; Wu et al., Biotherapy 3:87–95, 1991).

Alternatively, the protein may be introduced into a target cell by overexpressing within the cell a nucleic acid construct comprising a promoter sequence operably linked to a sequence encoding the protein. In this method, the nucleic acid construct is derived from a non-replicating linear or circular DNA or RNA vector, or from an autonomously replicating plasmid or viral vector; or the construct is integrated into the host genome.

Any vector that can transfect a hepatocyte may be used in the methods of the invention. Preferred vectors are viral vectors, including those derived from replication-defective hepatitis viruses (e.g., HBV and HCV), retroviruses (see, e.g., WO89/07136; Rosenberg et al., N. Eng. J. Med. 323 (9):570–578, 1990), adenovirus (see, e.g., Morsey et al., J. Cell. Biochem., Supp. 17E, 1993), adeno-associated virus (Kotin et al., Proc. Natl. Acad. Sci. USA 87:2211–2215, 1990), replication defective herpes simplex viruses (HSV; Lu et al., Abstract, page 66, Abstracts of the Meeting on Gene Therapy, Sep. 22–26, 1992, Cold Spring Harbor Laboratory, Cold Spring Harbor, N.Y.), and any modified versions of these vectors. Retroviruses are particularly useful since they typically target proliferating and not quiescent cells. Non-viral vectors, e.g., plasmid vectors, can also be used. In one such system, the plasmid forms a molecular conjugate with poly-L-lysine by electrostatic forces. Poly-L-lysine covalently bonds to a ligand that binds to a receptor on tumor cells (Cristiano et al., J. Mol. Med. 73:479–486, 1995).

Methods for constructing expression vectors are well known in the art (see, e.g., Molecular Cloning: A Laboratory Manual, Sambrook et al., eds., Cold Spring Harbor Laboratory, 2nd Edition, Cold Spring Harbor, N.Y., 1989; Current Protocols in Molecular Biology, Ausubel et al., eds., John Wiley & Sons, Inc., 1995).

In these vectors, promoters are operably linked to the nucleic acid sequence encoding an inhibitory protein of the invention. Any promoter that can direct a high level of transcription initiation in the target cells may be used in the invention. Non-tissue specific promoters, such as the cytomegalovirus (DeBernardi et al., Proc. Natl. Acad. Sci. USA 88:9257–9261, 1991, and references therein), mouse metallothionine I (Hammer, et al., J. Mol. Appl. Gen. 1:273–288, 1982), HSV thymidine kinase (McKnight, Cell 31:355–365, 1982), β-actin, and SV40 early (Benoist et al., Nature 290:304–310, 1981) promoters may be used in the invention. However, preferred in the invention are tissue-specific (e.g., hepatocyte-specific) promoters, the use of which ensures that the proteins are expressed primarily in the target tissue (e.g., liver). Exemplary hepatocyte-specific promoters are the albumin, α-fetoprotein, alpha-1-antitrypsin, retinol-binding protein, and asialoglycoprotein receptor promoters. Viral promoters and enhancers that include those derived from herpes simplex viruses (types I and II), hepatitis viruses (A, B, and C), and Rous sarcoma virus (RSV; Fang et al., Hepatology 10:781–787, 1989) may also be used in the invention.

The above-described nucleic acid constructs and vectors can be introduced into target cells as naked DNA, or by liposome fusion or erythrocyte ghosts. Alternatively, the nucleic acid constructs can be coupled to ligands of tissue-specific receptors, and thereby enter the target cells via receptor-mediated endocytosis. For example, one could use a ligand which binds the hepatic asialoglycoprotein receptor, such as asialo-oromucoid or (poly)L-lysine-asialo-orosomucoid. Alternatively, one can employ a viral-based vector as a means for introducing the nucleic acid into hepatocytes.

The inhibitory proteins of the invention can be produced in commercially significant amounts by recombinant methods employing cultured cells. The cells can be prokaryotes (e.g., E. coli) or eukaryotes (e.g., yeast, insect cells, or mammalian cells). The nucleic acid molecules encoding the inhibitory proteins and having appropriate expression control sequences can be introduced into the cultured cells by viral infection, receptor-mediated endocytosis, liposome fusion, biolistic transfer, electroporation, calcium phosphate precipitation, DEAE-Dextran transfection, or any other standard transfection technique. Extraction and purification of recombinant proteins produced by the transfected cells can be performed with techniques well known in the art, including, for example, immunoaffinity purification.

Therapeutic compositions containing the inhibitory proteins or nucleic acid molecules encoding these proteins can be administered to a patient with hepatocarcinoma, or prophylactically to a patient who, e.g., is infected with hepatitis B or C virus but has not yet shown symptoms of hepatocarcinoma. The therapeutic compositions of the invention may be used alone or in a mixture, or in chemical combination, with one or more materials, including cancer chemotherapeutics, other proteins or recombinant vectors that increase the biological stability of the proteins or the recombinant vectors, or agents that increase the therapeutic compositions' ability to penetrate hepatocytes selectively. The therapeutic compositions of the invention may be administered in a pharmaceutically acceptable carrier (e.g., physiological saline), which is selected on the basis of the mode and route of administration, and standard pharmaceutical practice. Suitable pharmaceutical carriers, as well as pharmaceutical necessities for use in pharmaceutical formulations, are described in *Remington's Pharmaceutical Sciences*, a standard reference text in this field, and in the USP/NF.

The therapeutic compositions of the invention can be administered in dosages determined to be appropriate by one skilled in the art. It is expected that the dosages will vary, depending upon the pharmacokinetic and pharmacodynamic characteristics of the particular agent, and its mode and route of administration, as well as the age, weight, and health (including renal and hepatic function) of the recipient; the nature and extent of the disease; the frequency and duration of the treatment; the type of, if any, concurrent therapy; and the desired effect. It is expected that a useful dosage contains between about 0.1 to 100 mg of active ingredient per kilogram of body weight. Ordinarily, 0.5 to 50 mg, and preferably 1 to 10 mg of active ingredient (nucleic acid or protein) per kilogram of body weight per day, given in divided doses or in sustained release form, is appropriate. If the protein or nucleic acid is delivered locally to the site of the tumor, a smaller dose can be used.

The therapeutic compositions of the invention may be administered to a patient by any appropriate mode, e.g., parenterally, intraperitoneally, or intravenously, as determined by one skilled in the art. Alternatively, it may be desired to administer the treatment surgically to the target tissue, e.g., by implantation of a biodegradable capsule. The treatments of the invention may be repeated as needed, as determined by one skilled in the art.

The mutants of the invention can also be used in studies of the insulin/IGF-1 signal transduction pathway and its relationship with other signal transduction pathways in mammalian cells. For instance, a mutant of the invention can be used to block the insulin-activated signal transduction pathway in a cell, so that alternative signal transduction pathways in the cell can be studied. Methodology used for such studies is well known in the art of signal transduction.

The following example is meant to illustrate the methods and materials of the present invention. Suitable modifications and adaptations of the described conditions and parameters which are obvious to those skilled in the art are within the spirit and scope of the present invention.

EXAMPLE

Materials and Methods

Reagents and Cells

FOCUS is a poorly differentiated human cell line derived from a HBV (hepatitis B virus) positive hepatocellular carcinoma tumor (Nishiyama et al., *Biochem. Biophys. Res. Commun.* 183:280–285, 1992). The FOCUS cells were employed as a source of mRNA for a cDNA library used to clone the hIRS-1 cDNA. HepG2 (hepatoblastoma) cells, which are well differentiated, were cultured in Dulbecco's modified Eagle's media (DMEM; Mediatech) supplemented with 10% heat-inactivated fetal bovine serum (FBS; Sigma), and HuH-7 HCC cells, which are moderately differentiated, were cultured in RPMI medium 1640 (Mediatech) supplemented with 30 nM $Na_2SeO_3$ (serum free) or with 10% FBS.

For immunoprecipitation and immunoblot studies, anti-IRS-1 rabbit polyclonal antibody (Upstate Biotechnology), anti-phosphotyrosine antibody conjugated to horseradish peroxidase (PY20H; Transduction Laboratories), anti-Shc rabbit polyclonal antibody (Transduction Laboratories), anti-insulin receptor rabbit polyclonal antibody (provided by Dr. X. F. Zhang), anti-FLAG M2 mouse monoclonal antibody (Kodak), anti-Grb2 rabbit polyclonal antibody (Santa Cruz Biotechnology), anti-Syp/PTP2C mouse monoclonal antibody (Transduction Laboratories) and anti-p85 PI3K rabbit polyclonal antibody (Upstate Biotechnology Inc.) were employed. Mitogen-activated protein kinase (MAPK) activity was measured using myelin basic protein (MBP; Sigma) as a specific substrate.

Construction of hIRS-1 Mutants

DNAs encoding various hIRS-1 deletional mutants were sequentially constructed using PCR or restriction enzyme digestion. A FLAG epitope (DYKDDDDK; SEQ ID NO:5) was added to the C-terminus by PCR. Each cDNA was subcloned into the pCDNA3 plasmid (Invitrogen) between the CMV promoter and the SV40 poly A region. The nucleotide sequences of the DNAs were confirmed by sequencing with Sequenase 2.0 (United States Biochemical Inc.).

Cell Culture and Transfection Studies

Parental FOCUS cells, HepG2 cells, and HCC transfectants (He et al., In *Vitro* 20:493–504, 1984) were cultured in DMEM supplemented with 10% heat-inactivated FBS. HCC cells ($1 \times 10^6$) grown in 3.5 cm petri dishes were transfected with 2 µg of one of the various hIRS-1 mutant constructs or the pcDNA3 vector alone (mock) using Lipofectamine (Life Technologies, Inc.) according to manufacturer's instructions. Two days after transient transfection, cells were serum starved for 12 hr, and then treated with 100 nM insulin. To select for stable transfectants, transfected cells were split 1:10 and grown in the presence of 800 µg/ml G418. Resistant colonies were isolated.

Immunoblot and Immunoprecipitation Analysis

HCC transfectants were serum starved for 24 hr, and then treated with insulin, IGF-1 or EGF-1. The cells were subsequently lysed in a Triton-lysis buffer containing 50 mM Tris-HCl (pH 7.5), 1% Triton, 2 mM EGTA, 10 mM EDTA, 100 mM NaF, 1 mM $Na_4P_2O_7$, 2 mM $NaVO_4$, 1 mM phenylmethylsulfonyl fluoride, 25 mg/ml aprotinin, 3.5 mg/ml pepstatin A, and 25 mg/ml leupeptin. Cell lysates containing about 100 µg of total protein were electrophoresed on SDS-polyacrylamide gel, and analyzed by Western blot analysis using Immobilon-P membrane (Millipore Corp.). For immunoprecipitation studies, cell lysates containing about 500 µg of protein were incubated with specific antibodies and precipitated with protein A-agarose beads. The immunoprecipitates were subjected to SDS-polyacrylamide gel electrophoresis, and analyte proteins were detected with specific antibodies.

Mitogenic and Anchorage-Independent Growth Assays

HCC cells transfected with the various IRS-1 constructs were plated at a concentration of $1 \times 10^5$ cells in 24-well plates. Twenty-four hours later, the medium was replaced with DMEM containing 0.25% FBS. Cells were incubated with or without 100 nM insulin or 100 ng/ml IGF-1 for 18 hr, and pulse-labeled with 1 mCi/ml [$^3$H]-thymidine in DMEM for 3 hr. The labeled cells were washed, and re-suspended in 1 ml of PBS containing 0.1% SDS and 10% trichloroacetic acid (TCA). The TCA-insoluble cell pellet was solubilized in 1 N NaOH and neutralized with HCl. The amount of [$^3$H]-thymidine incorporated into DNA was determined by liquid scintillation counting.

The ability of transfected cells to exhibit anchorage-independent growth was determined by plating 1×10³ cells in DMEM containing 10% FBS and 0.4% soft agar (FMC Bioproducts). The DMEM/FBS/agar medium was overlaid on a bottom agar medium containing DMEM, 10% FBS and 0.53% agar. Anchorage-independent growth of the parental and clonal stable transfectants was assessed by counting the number of colonies formed in soft agar 2 weeks after seeding.

Tumor Formation in Nude Mice

To investigate tumorigenicity of the HCC transfectants, 1×10⁷ cells of the parental (i.e., transfected with mock plasmid DNA) and ΔChIRS-1 FOCUS HCC cell clones in 0.1 ml PBS were injected subcutaneously into the backs of nude mice. The mice were observed for 4 weeks, and solid tumor formation was determined.

MAPK and PI3K Assays

Insulin or IGF-1-induced MAPK and PI3K activation was measured using cell lysates derived from transfected cells that had been incubated with or without 100 nM insulin or 100 ng/ml IGF-1 for 10 min after 24 hr of serum starvation. MAPK enzymatic activity was measured as previously described (Baltensperger et al., $Science$ 260:1950–1952, 1993). Briefly, lysates of cells with or without hormone stimulation were electrophoresed on SDS-polyacrylamide gel containing 0.5 mg/ml MBP. SDS was subsequently removed from the gel by washing the gel with 50 mM Tris-HCl (pH 8.0) containing 20% 2-propanol for 1 hr and then with 50 mM Tris-HCl (pH 8.0) containing 5 mM 2-mercaptoethanol for an additional hour at 20° C. MAPK in the gel was denatured by treatment with 6M guanidine HCl and 50 mM Tris-HCl (pH 8.0) for 1 hr at 20° C., and renatured in 50 mM Tris-HCl (pH 8.0) containing 0.04% Tween-40 and 5 mM 2-mercaptoethanol. The gel was then incubated in a kinase buffer [40 mM HEPES (pH 8.0), 2 mM dithiothreitol, 0.1 mM EGTA, 20 mM $MgCl_2$] for 1 hr at 25° C. Phosphorylation of MBP was performed by incubating the gel with a kinase buffer containing 25 μCi of [γ-³²P] ATP (Dupont) for 1 hr at 25° C. The gel was washed in 5% (w/v) TCA solution containing 1% sodium pyrophosphate. MAPK-induced phosphorylation of MBP was determined by autoradiography.

To measure PI3K activity, 500 μg of cell lysate was immunoprecipitated with polyclonal antibody against the p85 subunit of PI3K, and then incubated with protein A-SEPHAROSE beads. The immunoprecipitates were washed twice with cell lysis buffer, once with 1% NP40-PBS, once with 100 mM Tris-HCl (pH 7.4) containing 0.5 M LiCl, and twice with 10 mM Tris-HCl containing 100 mM NaCl. Samples were preincubated with a phosphoinositol (PI) solution (sonicated PI, 50 mM HEPES, 1 mM EGTA, 1 mM sodium phosphate) and then reacted with 1 μCi of [γ-³²P] ATP, 50 mM ATP and 10 mM $MgCl_2$ for 10 minutes. After termination of the reaction with HCl and $CHCl_3$/methanol mixture, lipid phosphorylation was analyzed by thin-layer chromatography on silica gel plates coated with 1% potassium oxalate. Radioactive signals on the gel plates were visualized by autoradiography.

Results

The N-terminus of hIRS-1 is Required for Its Tyrosyl Phosphorylation in HCC Cells To determine the regions of hIRS-1 required for its TP in FOCUS cells, DNA constructs expressing N-terminal (designated hIRS-1Δ3-516 or ΔN-hIRS-1) and C-terminal (designated hIRS-1Δ517-1243 or ΔC-hIRS-1) truncated mutants of hIRS-1, each of which contained a FLAG epitope at its C-terminus, were made (FIG. 1) and transiently transfected into FOCUS cells. Both hIRS-1 mutants have numerous potential TP sites in their sequences (Myers et al., $Trends Biochem. Sci.$ 19:289–293, 1994; Sun et al., $Nature$ 377:173–177, 1995). Western blot analysis demonstrated that, following transfection of hIRS-1Δ3-516 and hIRS-1Δ517-1243 constructs into HCC cells, the mutant proteins were expressed with the predicted molecular size (approximately 100 kD and 60 kD, respectively) as determined by a C-terminal specific antibody and anti-FLAG M2 antibody. Western blot analysis using an anti-phosphotyrosine antibody (aPY) revealed that insulin stimulation caused TP in hIRS-1Δ517-1243 but not in hIRS-1Δ3-516. TP of hIRS-1Δ517-1234 was highly prominent in FOCUS transfectants. TP of hIRS-1Δ517-1243 was also apparent in another transiently transfected HCC cell line, HepG2. These results show that at least a portion of the amino-terminal 516 residues of hIRS-1 is required for insulin-stimulated TP of hIRS-1 in both FOCUS and HepG2 HCC cell lines.

TP of ΔC-hIRS-1 Requires the First PTB Domain

The N-terminus of hIRS-1 is composed of three functional domains: a pleckstrin homology (PH) domain and two PTB domains. To address the role of these domains in TP, constructs encoding hIRS-1 mutants with sequential truncations of these domains (FIG. 1) were prepared. The FOCUS cells were stably transfected with each mutant construct and 2 to 4 neomycin-resistant transfectant clones were established for each construct. Each mutant protein has potential TP sites in its sequence (Myers et al., $Trends Biochem. Sci.$ 19:289–293, 1994; Sun et al., $Nature$ 377:173–177, 1995). Western blot analysis using anti-FLAG M2 antibody confirmed that progressive truncation of these domains reduced the size of the expressed protein. Western blot analysis using aPY showed that TP of ΔC-hIRS-1, ΔC-hIRS-1Δ9-117, ΔC-hIRS-1Δ163-256, and ΔC-hIRS-1Δ9-117Δ320–457 mutant proteins was evident in insulin-stimulated FOCUS cells, whereas AC-hIRS-1163–256, ΔC-hIRS-1Δ119-457, and ΔC-hIRS-1Δ4-296 mutant proteins were not tyrosyl phosphorylated to any appreciable extent. There was no change in the level of expression of the insulin receptor or endogenous hIRS-1 protein in all stable transfected and cloned cell lines. These studies demonstrate that the most amino-terminal PTB domain is required for TP of ΔC-hIRS-1 in FOCUS HCC cells.

ΔC-hIRS-1 inhibits insulin- and IGF-1-induced TP of endogenous hIRS-1

Subsequent to insulin (100 nM) stimulation for 5 minutes, the 180–190 kDa endogenous hIRS-1 protein was tyrosyl-phosphorylated in FOCUS cells transfected with mock plasmid DNA. However, in FOCUS cells stably transfected with ΔC-hIRS-1, the TP of endogenous hIRS-1 (immunoprecipitated by anti-hIRS-1 antibody) was substantially decreased, while the expressed ΔC-hIRS-1 mutant protein (immunoprepicitated by M2 antibody) was highly tyrosyl-phosphorylated. Endogenous hIRS-1 was rapidly dephosphorylated within 2 hr in insulin-deprived FOCUS cells transfected with mock plasmid DNA. The tyrosyl-phosphorylated ΔC-hIRS-1 protein was not dephosphorylated as rapidly as endogenous hIRS-1, and high levels of phosphorylation were observed after 8 hr of insulin deprivation. The dominant negative effect of ΔC-hIRS-1 on TP of endogenous hIRS-1 was not observed with other hIRS-1 mutant proteins (e.g., ΔC-hIRS-1Δ9-117, ΔC-hIRS-1Δ163-256, ΔC-hIRS-1Δ320-457, ΔC-hIRS-1Δ119-457, ΔC-hIRS-1Δ9-117Δ320-457, and ΔC-hIRS-1Δ4-296).

Notably, the ΔC-hIRS-1 protein co-immunoprecipitated with the β subunit of the insulin receptor, suggesting that the mutant molecule binds and occupies the insulin receptor. In this experiment, cells from two different clones of the ΔC-hIRS-1 transfectant were treated with or without insulin, and cell lysates of these cells were immunoprecipitated with an anti-insulin receptor antibody. The immunoprecipitates were immunoblotted with an anti-FLAG antibody (aIR/aFLAG) to detect the ΔC-hIRS-1 mutant protein in the immunoprecipitate. Other tyrosyl-phosphorylated mutant proteins were found not to co-immunoprecipitate with the β subunit of the insulin receptor.

Insulin and IGF-1 also stimulated TP of Shc in FOCUS cells transfected with mock plasmid DNA. Stable FOCUS transfectants of ΔC-hIRS-1 (i.e., cell lines c1 and c2) showed a striking suppression of insulin- and IGF-1-induced TP of Shc. However, expression of ΔC-hIRS-1 did not affect TP of Shc induced by EGF stimulation. The result indicates that ΔC-hIRS-1 overexpression in HCC cells specifically inhibits insulin- and IGF-1-induced TP of endogenous cellular substrates in addition to hIRS-1.

Tyrosyl phosphorylation of endogenous hIRS-1 induced by insulin or IGF-1 leads to the activation of downstream molecules (such as MAPK and PI3K) which are involved in the signal transduction cascade. However, in FOCUS cells stably transfected with ΔC-hIRS-1, insulin-induced activation of MAPK and PI3K was diminished to levels found in non-insulin stimulated cells.

[$^3$H]-thymidine incorporation into DNA was measured in stable FOCUS transfectants in order to assess the effects of the various hIRS-1 mutants on insulin- and IGF-stimulated DNA synthesis. [$^3$H]-thymidine incorporation in response to insulin/IGF-1 treatment was increased approximately three-fold in cells transfected with mock plasmid DNA. However, in each of the two ΔC-hIRS-1-transfected clones studied (i.e., c1 and c2), [$^3$H]-thymidine incorporation following insulin or IGF-1 treatment remained at a level similar to that of cells not treated with the hormone (i.e., quiescent cells). [$^3$H]-thymidine incorporation was not substantially inhibited in FOCUS cell lines stably transfected with the other mutant constructs.

ΔC-hIRS-1 expression changes the characteristics of the malignant phenotype

Parental FOCUS cells exhibit characteristics of the malignant phenotype including anchorage independent cell growth (Barrett et al., *Proc. Natl. Acad. Sci. USA* 75:3761–3765, 1978; He et al., In *Vitro* 20:493–504, 1984). As shown in Table 1, FOCUS cells transfected with mock plasmid DNA formed colonies in soft agar. However, individual clones derived from ΔC-hIRS-1 transfected FOCUS cells demonstrated very low efficiency of colony formation in soft agar, indicating the loss of the capacity for anchorage independent cell growth. Cloned cell lines transfected with other mutant hIRS-1 constructs all retained to a significant degree the ability to grow in an anchorage-independent manner.

Parental FOCUS cells are poorly differentiated, and exhibit a large irregular flattened shape, multiple mitotic figures, and pleomorphic nuclei with prominent nucleoli. FOCUS cells transfected with mock plasmid DNA retained these characteristics. Like parental cells, the mock transfected cells grew rapidly without contact inhibition and formed multi-layered structures when they reached confluence. In contrast, stable transfection with ΔC-hIRS-1 substantially altered the morphological appearance of the FOCUS cells. The cloned cell lines c1 and c2 exhibited differentiated morphology such as sinusoid formation, and in addition exhibited contact inhibition of cell growth. These cells, which were much smaller than parental cells and had a polygonal morphology with normal-appearing nuclei, had an appearance reminiscent of adult hepatocytes in primary cultures (Bissell et al., *J. Clin. Invest.* 79:801–812, 1987).

A similar alteration of phenotype was also observed in HuH-7 cells stably transfected with ΔC-hIRS-1. HuH-7 cells were derived from a human tumor not related to chronic HBV infection, and can be grown under serum free conditions (Nakabayashi et al., *Cancer Res.* 42:3858–3863, 1982). Following treatment with 100 ng/ml IGF-1, expression and TP of ΔC-hIRS-1 were observed in cells of stably transfected HuH-7 cell lines h1 and h2. Expression of ΔC-hIRS-1 inhibited IGF-1-induced TP of endogenous hIRS-1. HuH-7 cells transfected with mock plasmid DNA had a pleomorphic and fibroblastoid appearance in a serum-free medium as well as in a medium containing 10% FBS. H1 and h2 cells, however, demonstrated a differentiated polygonal cellular morphology and formed flat sheets of cells, exhibiting contact inhibition with a sinusoidal growth pattern reminiscent of adult hepatocytes in culture.

Finally, the ability of parental and transfected FOCUS cells to form solid tumors was assessed in nude mice as previously described (He et al., In *Vitro* 20:493–504, 1984). $1 \times 10^7$ FOCUS cells transfected with mock plasmid DNA were injected subcutaneously into nude mice, and rapid tumor formation was observed at the injection site. The tumors reached a mean size of 2.5 cm within 28 days in 9 of 10 injected mice. In contrast, none of the mice injected with c1 or c2 cells developed tumors (Table 2).

TABLE 1

Anchorage-independent growth of FOCUS transfectants

| Clone | Efficiency of colony formation in soft agar (%)* |
|---|---|
| mock | 7.1 ± 0.5 |
| ΔC-hIRS-1 c1 | 0.2 ± 0.1 |
| ΔC-hIRS-1 c2 | 0.1 ± 0.1 |
| ΔC-hIRS-1Δ9-117 c1 | 4.3 ± 1.1 |
| ΔC-hIRS-1Δ9-117 c2 | 3.6 ± 0.7 |
| ΔC-hIRS-1Δ163-256 c1 | 6.8 ± 1.0 |
| ΔC-hIRS-1Δ163-256 c2 | 7.2 ± 0.8 |
| ΔC-hIRS-1Δ320-457 c1 | 4 0 ± 0.6 |
| ΔC-hIRS-1Δ320-457 c2 | 3.1 ± 0.3 |
| ΔC-hIRS-1Δ119-457 c1 | 8.2 ± 1.1 |
| ΔC-hIRS-1Δ119-457 c2 | 7.6 ± 1.3 |
| ΔC-hIRS-1Δ9-117Δ320–457 c1 | 5.1 ± 0.5 |
| ΔC-hIRS-1Δ9-117Δ320–457 c2 | 4.2 ± 0.4 |
| ΔC-hIRS-1Δ4–296 c1 | 6.6 ± 0.9 |
| ΔC-hIRS-1Δ4–296 c2 | 7.1 ± 0.8 |

*Efficiency of colony formation is represented by percentage of cells that formed colonies in each well. The data were obtained from duplicate experiments.

TABLE 2

Tumor formation by FOCUS transfectants

| Clone | Tumors/mice* |
|---|---|
| mock plasmid | 9/10 |
| ΔC-hIRS- 1 c1 | 0/9 |
| ΔC-hIRS- 1 c2 | 0/9 |

*Tumorigenicity was determined by subcutaneous injection of $1 \times 10^7$ cells into nude mice and measurement of tumor size at week 4 after injection.

Other Embodiments

It is to be understood that while the invention has been described in conjunction with the detailed description thereof, that the foregoing description is intended to illustrate and not limit the scope of the invention, which is defined by the scope of the appended claims.

Other aspects, advantages, and modifications are within the scope of the following claims.

What is claimed is:

1. A dominant negative mutant polypeptide of a mammalian insulin receptor substrate-1 (IRS-1), wherein the mutant polypeptide comprises a pleckstrin homology domain and at least one phosphotyrosine binding domain, and does not bind to any Src homology domain 2 (SH2) of Syb, Grb2, PI3K, and NCK.

2. The mutant polypeptide of claim 1, wherein the mutant polypeptide comprises two phosphotyrosine binding domains of said IRS-1.

3. The mutant polypeptide of claim 1, wherein the mammalian IRS-1 is a human IRS-1.

4. The mutant polypeptide of claim 1, wherein the mammalian IRS-1 is a human IRS-1, and the mutant polypeptide comprises 460 amino acid residues from the amino-terminal half of the human IRS-1, and lacks at least 300 amino acid residues from the carboxy-terminal half of the human IRS-1.

5. The mutant polypeptide of claim 1, wherein the mutant polypeptide further comprises a heterologous sequence 4–25 amino acid residues in length, said heterologous sequence comprising an epitope to which an antibody binds.

6. The mutant polypeptide of claim 4, wherein the mutant polypeptide comprises 516 amino acid residues from the amino-terminal half of the human IRS-1, and lacks amino acid residues 517–1243 from the carboxy-terminal half of the human IRS-1.

* * * * *